United States Patent [19]

Kim et al.

[11] 4,317,936
[45] * Mar. 2, 1982

[54] HYDROFORMYLATION PROCESS USING RESIN-LIGAND-METAL CATALYST

[75] Inventors: Leo Kim; Timm E. Paxson, both of Houston; Sunny C. Tang, Katy, all of Tex.

[73] Assignee: Shell Oil Company, Houston, Tex.

[*] Notice: The portion of the term of this patent subsequent to Dec. 15, 1998, has been disclaimed.

[21] Appl. No.: 66,350

[22] Filed: Aug. 13, 1979

Related U.S. Application Data

[60] Continuation-in-part of Ser. No. 55,225, Jul. 5, 1979, abandoned, which is a division of Ser. No. 905,813, May 15, 1978, Pat. No. 4,179,402.

[51] Int. Cl.$^3$ .................. C07C 45/50; C07C 27/22
[52] U.S. Cl. .................. 568/454; 568/882; 568/909; 252/431 P; 568/455
[58] Field of Search .................. 260/604 HF; 568/909, 568/454, 882, 455; 252/431 P, 431 N

[56] References Cited

U.S. PATENT DOCUMENTS

| | | | |
|---|---|---|---|
| 3,239,566 | 3/1966 | Slaugh et al. | 260/604 HF |
| 3,825,601 | 7/1974 | Rennick | 260/604 HF |
| 3,847,997 | 11/1974 | Allen | 260/604 HF |
| 3,929,898 | 12/1975 | Neinburg et al. | 260/604 HF |
| 3,954,883 | 5/1976 | Haag et al. | 260/604 HF |
| 3,994,978 | 11/1976 | Whitehurst | 260/604 HF |
| 3,998,864 | 12/1976 | Trevillyan | 260/604 HF |
| 4,098,727 | 3/1979 | Hartwell | 260/604 HF |
| 4,144,191 | 3/1979 | Hartwell | 260/604 HF |

OTHER PUBLICATIONS

Pittman et al., "Chemtech", Sep., (1973), pp. 560–566.

*Primary Examiner*—Werren B. Lone

[57] ABSTRACT

The hydroformylation of olefinic hydrocarbons is effected by treating the hydrocarbon with hydrogen and carbon monoxide in the presence of a catalyst comprising an ion exchange resin, a metal selected from the group consisting of cobalt, ruthenium, palladium, platinium, and rhodium bound to said resin and an organic linking compound which has at least one moiety which is ionically bonded to said resin and which further has at least one moiety which is coordinately bonded to said metal.

10 Claims, No Drawings

4,317,936

HYDROFORMYLATION PROCESS USING RESIN-LIGAND-METAL CATALYST

This application is a continuation-in-part of application Ser. No. 055,225 filed July 5, 1979, now abandoned, which is a divisional of application Ser. No. 905,813 filed May 15, 1978, which issued as U.S. Pat. No. 4,179,403 on Dec. 18, 1979.

BACKGROUND OF THE INVENTION

1. Field of the Invention

This invention relates to a process for hydroformylating olefins to alcohols and/or aldehydes utilizing a catalyst comprising an ion exchange resin with a ligand ionically bonded thereto with the ligand coordinately bonded to a transition element and with the transition element also bonded to the resin. The transition element is preferably cobalt, ruthenium, palladium, platinum or rhodium.

2. Background of the Invention

The use of heterogeneous catalysts over homogeneous catalysts has several advantages such as allowing the use of fixed beds, ease of separation of catalyst from the product and catalyst recovery and regeneration.

Traditionally, to produce heterogeneous catalysts from metals of the transition element series, these metals have been deposited on inert supports such as alumina or silica. More recently, metal catalysts have been covalently attached to inert resin backbones by use of diphenylphosphine or other ligands which are attached directly to the polymer and coordinately bonded to the metal. Typical examples of this type are found in U.S. Pat. No. 3,998,864, issued Dec. 21, 1976, and in Pittman et al, Chemtech, p. 560-566, 1973.

Application Ser. No. 861,916, filed Dec. 19, 1977, disclosed a composition comprising an ion exchange resin with an organic linking compound ionically bonded thereto and with the linking compound further coordinately bonded to a transition element metal. The composition of this invention, on the other hand, not only has the transition element bonded to the linking compound but also to the resin. This dual bonding of the metal provides additional stability. The composition utilized in the process of this invention is much more leach resistant with regard to the transition metal than conventional heterogeneous transition metal catalysts. The materials utilizing this invention are also relatively simple to prepare using commercially available compounds. Their preparations involve no exotic conditions and often times may be carried out in an aqueous solvent system and the resins may be easily stripped of metal and ligands for isolation of the metal species and regeneration of the catalyst. The resin based catalysts utilized in this invention have unique selectivity-reactivity properties when compared to their homogeneous analogues.

SUMMARY OF THE INVENTION

This invention provides a process for hydroformylating olefins which comprises treating said olefins with carbon monoxide and hydrogen at hydroformylation conditions in the presence of a novel heterogeneous catalyst comprising (a) an ion exchange resin, (b) a metal selected from the group consisting of cobalt, ruthenium, palladium, platinum and rhodium and which is directly bonded, either coordinately or ionically, to the ion exchange resin and in addition (c) a linking compound which has at least one moiety coordinately bonded to the metal and further has at least one moiety which is ionically bonded to the ion exchange resin. The catalysts have unique selectivity-reactivity properties when compared to their homogeneous analogues and can easily be stripped of their expensive metal component and readily regenerated for further use.

DESCRIPTION OF THE PREFERRED EMBODIMENTS

Processes directed to the production of reaction mixtures comprising aldehydes and/or alcohols by the reactin of olefinic compounds with carbon monoxide and hydrogen at elevated temperatures and pressures in the presence of certain catalysts are well known in the art. The aldehydes and alcohols produced generally correspond to the compounds obtained by the addition of a carbonyl or carbinol group to an olefinically unsaturated carbon atom in the starting material with simultaneous saturation of the olefin bond. Isomerization of the olefin bond may take place to varying degrees under certain conditions with the consequent variation in the products obtained. These processes known in the industry, and referred to herein as hydroformylation, involve reactions which may be shown in the general case by the following equation:

$$R_1-\underset{R_2}{C}=\underset{R_3}{C}-R_4 + CO + H_2 \xrightarrow[\Delta]{\text{catalyst}} R_1-\underset{}{CH}-\underset{R_4}{\overset{R_3}{C}}-CHO$$

and/or $$R_1-\underset{}{CH}-\underset{R_4}{\overset{R_3}{C}}-CH_2OH + \text{isomeric alcohols and aldehydes}$$

In the above equation, each R represents an organic radical, for example, hydrocarbyl, or a suitable atom such as hydrogen or a halogen. The above reaction is similarly applied to an olefinic linkage in a cycloaliphatic ring.

In the past, dicobalt octacarbonyl as such or in several different forms, generally has been used as the catalyst for the hydroformylation of olefins. This catalyst, which can be prepared from many forms of cobalt, usually decomposes rapidly unless high pressures (1000-4500 psig) of carbon monoxide are maintained.

The hydroformylation of the unsaturated compound by treatment with carbon monoxide and hydrogen in the presence of the catalyst system of the present invention will be effected at hydroformylation conditions which include a temperature in the range of from about 40° to about 160° C., and preferably in a range of from about 60° to about 150° C. In addition, the reaction is also effected under superatmospheric pressures ranging from 1 up to about 500 atmospheres or more. The superatmospheric pressures are afforded by the introduction of gaseous carbon monoxide and hydrogen to the reaction zone or, if so desired, the pressure may be partially afforded by the carbon monoxide or hydrogen while the remaining pressure is afforded by a substantially inert gas such as nitrogen, helium or carbon dioxide although not necessarily with equivalent results.

Examples of suitable olefinic hydrocarbons which are utilized as a starting material in the hydroformylation process of this invention include, in particular, propylene, butene-1, butene-2, isobutene, pentene-1, pentene- 2, 2-methylbutene-1, 2-methylbutene-2, hexene-1, 3-methylpentene-1, 2-methylpentene-2, heptene-2, 2-methylhexene-2, 3-methylhexene-2, octene-1, octene-2, octene-3, heptene-1, nonene-1, decene-1, 3-methylheptene-1, 2-methylheptene-2, nonene-3, 3-methyloctene-2, decene-2, decene-5, decene-4, decene-3, 3,4-dimethyloctene-2, 4-ethyloctene-2, undecene-3, undecene-4, undecene-2, undecene-1, undecene-5, 4-methyldecene-2, 4,5-dimethylnonene-2, dodecene-1, dodecene-2, dodecene-3, dodecene-4, dodecene-5, tridecene-1, tridecene-2, tridecene-3, tetradecene-2, tetradecene-3, tetradecene-4, tetradecene-5, tetradecene-6, tetradecene-7, pentadecene-4, pentadecene-5, pentadecene-6, pentadecene-1, hexadecene-1, heptadecene-2, heptadecene-1, hexadecene-3, or mixtures of linear internal and terminal olefins such as internal olefins possessing carbon numbers between 11 and 14, 15 and 18 or 18 and 21, etc.

It is also contemplated within the scope of the process of the present invention that the hydroformylation may be effected in an inert organic medium as exemplified by n-pentane, n-hexane, n-heptane, n-octane, n-nonane, isooctane (2,2,4-trimethylpentane), cyclohexane, methylcyclohexane, benzene, toluene, m-xylene, mesitylene, etc.

It is understood that the aforementioned olefinic hydrocarbons and inert reaction mediums are only representative of the class of compounds which may be employed in the present hydroformylation invention and that the present invention is not necessarily limited thereto.

The desired products of the process of this invention, namely, alcohols and aldehydes, are utilized in the chemical industry in many ways. For example, alcohols are utilized in the synthesizing of other organic derivatives, as solvents, as an extraction medium, in dyes, synthetic drugs, synthetic rubbers, detergents, cleaning solutions, surface coatings, cosmetics, pharmaceuticals, in the preparation of esters, as a solvent for resin in coatings, in plasticizers, dyeing assistants, hydraulic fluids, detergent formulations and dehydrating agents. Aldehydes are utilized as perfumeries or precursors to perfumeries, or in the synthesis of primary alcohols. The non-linear alcohols and aldehydes are also utilized in the chemical industry in many other ways; for example, 2-methyl-1-butanol is utilized as a solvent in varnishes, lacquers and paint removers. Likewise, a general use of the non-linear alcohols and aldehydes is detergent formulations as exemplified by 2-butyl-1-heptanol.

The ratio of catalyst to the olefin to be hydroformylated is generally not critical and may vary widely within the scope of the invention. The ratio of catalyst to olefin charge may be varied to achieve a substantially homogeneous reaction mixture. Solvents are therefore not required. However, the use of solvents which are inert, or which do not interfere to any substantial degree with the desired hydroformylation reaction under the conditions employed, may be used within the scope of the invention. Saturated liquid hydrocarbons, for example, may be used as solvent in the process, as well as ketones, ethers, and the like. Molar ratios of catalyst to olefin between about 1:1000 and about 10:1 are found to be satisfactory; higher or lower catalyst to olefin ratios may, however, be used within the scope of the invention.

The ratio of hydrogen to carbon monoxide charged may vary widely within the scope of the invention. In general, a mole ratio of hydrogen to carbon monoxide of at least about 1 is employed. Suitable ratios of hydrogen to carbon monoxide comprises those within the range of from about 1 to about 10. Higher or lower ratios may, however, be employed within the scope of the invention. The ratio of hydrogen to carbon monoxide preferably employed will be governed to some extent by the nature of the reaction product desired. If conditions are selected that will result primarily in an aldehyde product, only one mole of hydrogen per mole of carbon monoxide enters into reaction with the olefin. When the alcohol is the desired product, two moles of hydrogen and one mole of carbon monoxide react with each mole of olefin. The minimum ratio of hydrogen to carbon monoxide employed will therefore generally be governed by the product desired. The use of ratios of hyrogen to carbon monoxide which are somewhat higher than those defined by these stoichiometrical values are generally preferred.

The ion exchange resins utilized to prepare the composition utilized in this invention are well known in the art and are readily available commercially. These are in the gel form or are macroporous and are either strongly acidic, weakly acidic, strongly basic, intermediate basic, weakly basic, or mixed acid-base. The strong acid resins typically have base resins of cross-linked styrene, styrene-divinylbenzene, phenol-formaldehyde, benzene-formaldehyde, having functional sulfonic or phosphonic acid groups attached thereto. Also suitable are the fluorinated alkyl sulfonic resins containing the —CFSO$_3$H groups as, for example, the NAFION® type resins supplied by E. I. DuPont DeNemours. The weak acid resins are those with carboxylic acid groups and are typically acrylic acid derivatives such as, for example, those resins prepared by the copolymerization of methacrylic acid and divinylbenzene. Another weak acid resin is the chelating type which is a styrene-divinylbenzene copolymer containing iminodiacetic acid functional groups which can serve as an anion exchanger at very low pH. The basic resins typically have base resins of cross-linked styrene, styrene-divinylbenzene, phenol-formaldehyde, benzene-formaldehyde, epoxypolyamine, phenolic-polyamine having functional amine, either primary, seconary, tertiary or quaternary, or pyridinium groups attached thereto. Typical examples of suitable commercially supplied resins are given in Table I (reference: Bio-Rad Laboratories Catalogue, Chromatography, Electrophoresis, Immunochemistry and Membrane Filtration, Price List C, March 1977, p. 11).

TABLE I

| Type and Exchange Group | Bio-Rad | Dow Chem. Company "Dowex" | Diamond-Shamrock "Duolite" | Rohm & Haas Co. "Amberlite" | Permutit Company (England) | Permutit Company (U.S.A.) |
|---|---|---|---|---|---|---|
| Anion exchange resins | | | | | | |
| Strongly Basic, polystyrene $\phi$-CH$_2$N$^+$(CH$_3$)$_3$Cl$^-$ | AG 1-X1 | 1-X1 | | | DeAcidite FF (lightly crosslinked) | S-100 |
| | AG 1-X2 | 1-X2 | | | | |
| | AG 1-X4 | 1-X4 | A-101D | IRA-401 | | |
| | AG 1-X8 | 1-X8 | | IRA-400 CG-400 | DeAcidite-FF | |
| | AG 1-X10 | 1-X10 | | IRA-425 | | |

TABLE I-continued

| Type and Exchange Group | Bio-Rad | Dow Chem. Company "Dowex" | Diamond-Shamrock "Duolite" | Rohm & Haas Co. "Amberlite" | Permutit Company (England) | Permutit Company (U.S.A.) |
|---|---|---|---|---|---|---|
| $\phi\text{-}CH_2N^+(CH_3)_2(C_2H_4OH)Cl^-$ | AG 21K<br>AG 2-X4<br>AG 2-X8<br>AG 2-X10<br>Bio-Rex 9 | 21K<br>2-X4<br>2-X8 | A-102D | IRA-402<br>IRA-410 | | S-200<br>A-580 |
| 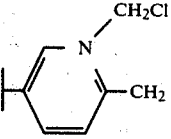 Intermediate Base, epoxypolyamine $R\text{—}N^+(CH_3)_2Cl^-$ and $R\text{—}N^+(CH_3)_2(C_2H_4OH)Cl^-$ | Bio-Rex 5 | | A-30B | | F | S-310<br>S-380 |
| Weakly Basic, polystyrene or phenolic polyamine $\phi\text{-}CH_2N^+(R)_2Cl^-$ | AG 3-X4 A | WGR | A-6<br>A-7<br>A-4F | IR-45<br>IR-4B<br>IRA-68 | G | S-300<br>S-350 |
| Cation exchange resins | | | | | | |
| Strong Acidic, phenolic $R\text{—}CH_2SO_3^-H^+$ | Bio-Rex 40 | | C-3 | | Zeocarb 215 | |
| Strong Acidic, polystyrene $\phi\text{-}SO_3^-H^+$ | AG 50W-X1<br>AG 50W-X2<br>AG-50W-X4<br>AG 50W-X8<br>AG 50W-X10<br>AG 50W-X12<br>AG 50W-X16 | 50W-X1<br>50W-X2<br>50W-X4<br>50W-X8<br>50W-X10<br>50W-X12<br>50W-X16 | C-20<br>C-20X10<br>C-20X12 | IR-116<br>IR-118<br>IR-120<br>CG-120<br>IR-122<br>IR-124 | Zeocarb 225(X4)<br>Zeocarb 225 | Permutit Q<br>Q-100<br>Q-110<br>Q-130 |
| Weakly Acidic, acrylic $R\text{—}COO^-Na^+$ | Bio-Rex 70 | | CC-3 | IRC-50<br>CG-50 | Zeocarb 226 | Q-210 |
| Weakly Acidic, chelating resin, polystyrene 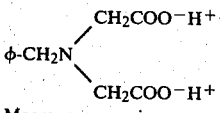 | Chelex 100 | A-1 | | | | |
| Macroporous resins | | | | | | |
| Strong Base, polystyrene $\phi\text{-}CH_2N^+(CH_3)_3Cl^-$ | AG MP-1 | MSA-1 | A-161 | IRA-900 | | |
| Strong Acid, polystyrene $\phi\text{-}SO_3^-H^+$ | AG MP-50 | MSC-1 | C-25D | 200 | | |
| Mixed bed resins | | | | | | |
| $\phi\text{-}SO_3^-H^+$ & $\phi\text{-}CH_2N^+(CH_3)_3OH^-$ | AG 501-X8 | | GPM-331 G | MB-1 | Bio-Demineralit | M-100 |

The preferred resin choice for the composition used in this invention will depend on the particular ionically bondable moiety utilized on the linking compound as well as on the particular use envisioned for the composition. For example, if the composition were used in liquid-phase catalysis, the composition and pH of the liquid would determine the preferred resin to be utilized.

The linking compound is hydrocarbyl, i.e., alkyl, aryl, or mixtures of aryl and alkyl components, which can be either cyclic or acyclic or mixtures thereof containing from 1 to about 100 carbon atoms, preferably from about 3 to about 80 carbon atoms and has at least two moieties containing an atom other than carbon.

At least one moiety is in the ionic or ionizable form and is compatible with the exchange group on the ion exchange resin, i.e., when the exchange group is acidic the resin-compatible ionic moiety on the linking compound is basic-derived and vice versa. The acidic-derived resin compatible ion moiety is derived from carboxylic acid ($RCO_2^-$), phosphonic acid ($RPO(OH)O^-$), phosphinic acid ($R_2POO^-$), sulfenic acid ($RSO^-$), sulfinic acid ($RSOO^-$), sulfonic acid ($RSO_2O^-$), boronic acid ($RB(OH)O^-$) boronous acid ($RBO^-$). The basic-derived resin compatible ion moiety is monohydrocarbyl ammonium ($RN^+H_3$), dihydrocarbyl ammonium ($R_2N^+H_2$), trihydrocarbyl ammonium ($R_3N^+H$), quaternary ammonium ($R_4N^+$), pyridinium ($RC_5H_4N^+R_1$), phosphonium ($R_4P^+$), arsonium ($R_4As^+$), and sulfonium ($R_3S^+$).

The linking compound may have more than one of the ionic moieties. It may be polyfunctional, for example, in carboxylate ion, in phosphonate ion, in sulfonate ion, in quaternary ammonium ion, in pyridinium and the like. The polyfunctional group may be the same or different.

At least one other moiety of the linking compound has an atom capable of complexing with metals from the transition element series, and consists of trivalent nitrogen, trivalent phosphorus, trivalent arsenic, trivalent bismuth, and trivalent antimony.

The three valences of the complexing atoms may be satisfied by any organic radical; saturated or unsaturated aliphatic, and/or saturated or unsaturated heterocyclic and/or aromatic radicals. These radicals may contain any functional group such as carbonyl, nitro, and hydroxy groups as well as saturated and unsaturated alkyl groups and the radical may be bonded to the complexing atom directly through a carbon-complexing atom linkage or through an electronegative atom such as oxygen or sulfur.

It is also suitable for a simple organic radical to satisfy more than one of the valences of the complexing atom, thereby forming a heterocyclic compound with the trivalent complexing atom. For example, an alkylene radical may satisfy two of the valences thereby forming a cyclic compound. Another example would be the alkylene dioxy radical to form a cyclic compound where oxygen atoms link an alkylene radical to the complexing atom. In these two examples, the third valence may be satisfied by any other organic radical.

The linking compound may have more than one of the metal-complexing moieties. It may be, for example, polydentate in phosphorus atom, e.g., it may be bi- or tridentate, having one or three phosphorus atoms. It may have mixed complexing atoms, e.g., a phosphorus and arsenic atom or two phosphorus atoms and one nitrogen atom, etc.

The trivalent nitrogen atom will be present as an amine, i.e., as a primary, secondary, tertiary, quaternary amine or as pyridine or cyanide. The trivalent phosphorus will be present as phosphine ($R_3P$), phosphinite ($ROPR_2$), phosphonite ($(RO)_2PR$) and phosphite ($(RO)_3P$). Correspondingly, trivalent arsenic will be available as arsine, arsinite, arsonite and arsenite; trivalent bismuth as bismuthine, bismuthinite, bismuthonite and bismuthite; and trivalent antimony as stibine, stibinite, stibonite and stibite. The preferred complexing atoms are phosphorus and nitrogen. The tertiary amines, phosphines, arsines and stibines and bismuthines have a marked tendency to form nonionic complexes with metals.

When the linking compound is polydentate is an ionizable heteroatom, it is understood that there will be a statistical distribution of the ionized atoms upon quaternization or protonation. For example, if one mole of a linking compound which contains 3 amine groups is protonated with 2 moles of HCl, then some of the molecules of the linking compound will have 3 quaternized amine groups, some will have 2 and some will have 1, but on the average there will be 2 quaternized amino groups per molecule. It is further understood from general principles of organic chemistry that unit charges resulting from quaternization and protonation can be distributed as partial charges over several heteroatoms in a linking compound molecule.

Thus the linking compound as reacted in the composition used in this invention will have at least one protonized or quaternized heteroatom and at least one heteroatom complexed with a transition element metal. Suitable linking compounds utilized in making the composition used in this invention include but are not limited to the following examples:
tris(dimethylamino)phosphine
tris(diethylamino)phosphine
tris(diisopropylamino)phosphine
tris(methylethylamino)phosphine
tris(p-dimethylaminophenyl)phosphine
tris(p-diethylaminophenyl)phosphine
tris(p-methylethylaminophenyl)phosphine
tris(o-dimethylaminophenyl)phosphine
tris(m-dimethylaminophenyl)phosphine
tris(dimethylaminoethyl)phosphine
tris(dimethylaminoethyl)phosphite
ethylbis(diphenylphosphinoethyl)amine Substitution of phosphinites, phosphonites, phosphites for the phosphine in the above compounds as well as arsines, arsinites, arsonites, arsenites, bismuthines, bismuthinites, bismuthonites, bismuthites, stibines, stibinites, stibonites, stibites and amines produces linking compounds useful in preparing the compositions used in this invention. Other suitable compounds are:
2-(P,P-diphenylphosphino)benzoic acid
tris(beta-aminoethyl)amine
2-chloronicotinic acid, and 2-caboxypyridine
1,1-dimethyl-4-phenylpiperazinium salt
2,2'-alkylarsino-1,1'-diphenylamine
2-(P,P-dicyclohexylphosphino)benzoic acid
beta-(dicyclohexylphosphino)propionic acid
1,4-(P,P-diphenylphosphino)benzene
2-diphenylphosphino-3-carboxy-2-butene
2-(P,P-diphenylphosphino)benzene sulfonic acid
2-amino-s-triazine
1-diphenylphosphino-2-diphenylphosphinoethane
tris-(N,N-diarylaminoethyl)phosphite
tris(N,N-diarylamino)phosphine
3-(dialkylphosphino)benzene phosphonic acid.

Thus, the organic linking compound is hydrocarbyl with at least one moiety capable of coordinate bonding and at least one moiety capable of ionic bonding. The primary limitation on the organic linking compound is a functional one, i.e., one moiety must be capable of coordinate bonding and the other moiety must be capable of ionic bonding. These moieties are well known to those skilled in the art.

The metals or metallic elements which are bonded to the ion exchange resin and also complexed with the linking compound are selected from the group consisting of cobalt, ruthenium, palladium, platinum and rhodium.

The complexed metals can be in various oxidation states. See "Complexes of the Transition Metals with Phosphines, Arsines and Stibines", by G. Booth, Adv. Inorg. Nucl. Chem., 6, 1–69 (1964) for a comprehensive description of complexes. For example, the Booth reference cites the following oxidation states for metals complexed with phosphines.

TABLE III

| Metal | Oxidation State for Stable Phosphine Complexes |
| --- | --- |
| Ru | 0, 2, 3, 4 |
| Co | 1, 2, 3 |
| Rh | 0, 1, 3 |
| Pd | 0, 2 |
| Pt | 0, 2 |

Articles dealing with the complexing of amines with metals are "Inorganic Complexes", Jorgensen, C.K., Academic Press 1963, chap. 4 and "Chemistry Coordination Compounds", Bailer (Ed.), Am. Chem. Soc. Monograph Series 131, 1956. The above references cite the following oxidation states for metals complexed with amines.

TABLE IV

| Metal | Oxidation State of Stable Amine Complexes |
|---|---|
| Ru | 2, 3 |
| Co | 2, 3 |
| Rh | 3 |
| Pd | 2 |
| Pt | 0, 2, 4 |

The metal is not only complexed with the linking compound but is also bonded directly to the ion exchange resin. The metal will be typically ionically bonded to the resin when the resin has acid functional groups attached thereto, such as for examples, sulfonic acid groups, phosphonic acid groups, fluorinated alkyl sulfonic acid groups, carboxylic acid groups, and iminodiacetic acid groups. Covalent bonding occurs when the ion exchange resin has basic functional groups attached thereto such as, for example, amino groups, either primary, secondary, tertiary or quarternary, or pyridinium groups or iminodiacetic acid groups.

The composition of the invention may have more than one transition element metal present. The composition may also have the metal(s) co-complexed with other ligands in addition to the linking compound. For example, from the above-noted Booth reference the metal complexed moiety of the composition could have the following form and still be within the scope of the invention, i.e., $M_y M_z' \cdot O_A H_B X_C (CN^-)_D (CO)_E (NO)_F (Cp)_G (Py)_H (Acac)_I (AsR_3)_J (NR_3)_K (PR_3)_L (SnX_3^-)_M (GeX_3^-)_M (Carb)_N P_Q (Funct.)_R$ $M_y$ = metal in oxidation state shown in Table II or Table III y=0 to n mononuclear to polynuclear cluster $M_z'$ = metal in oxidation state shown in Table II or Table III z=0 to n mononuclear or mixed metal polynuclear cluster where n is an integer greater than 0 when y>0 and z>0

O = oxygen where A = 0 to n
H = hydrogen where B = 0 to n
X = halide F, Cl, Br, I; where C = 0 to 5
(CN⁻) = cyanide where D = 0 to 5 when y+z=1 or D=1 to n when y+z>1
(CO) = carbonyl where E = 0 to 5 when y+z=1 or E=1 to n when y+z>1
(NO) = nitrosyl where F = 0 to 5 when y+z=1 or F = 1 to n when y+z>1
Cp = cyclopentadienyl where G=0 to 3 when w=z=1 or G=1 to n when y+z>1
Py = pyridine where H=0 to 5 when y+z=1 or H=1 to n when y+z>1
Acac = acetylacetonate where I=0 to 3 when y+z=1 or I=1 to n when y+z>1
(AsR₃) = arsines, where R=H, alkyl or aryl and J=0 to 5 when y+z=1 or J=1 to n when y+z>1 the arsine also may be of the chelating type or contain mixed donating atoms e.g.

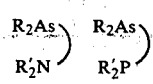

(NR₃) = amines, where R=H, alkyl, or aryl and K=0 to 5 when y+z=1 or K=1 to n when y+z>1 as with arsines, a chelating or mixed donor chelating ligand may be employed.

(PR₃) = phosphines were R=H, alkyl, or aryl, and L=0 to 5 when y+z=1 or L=1 to n when y+z>1 as with arsines, and amines, a chelating ligand may be employed.

(SnX₃⁻) or (GeX₃⁻) = trihalostannyl or trihalogermyl where X=F, Cl, Br, I and M=0 to 5 when y+z=1 or M=1 to n when y+z>1

(Carb) = carboxylate where N=0 to 5 when y+z=1 or N=1 to n when y+z>1

P = the bridging moiety/ligand between the metal and the resin support and Q=1 to n.

(Funct.) = functional ion exchange group attached to the ion-exchange resin and R=1 to n.

In general terms, this invention is a process for hydroformylating olefins which comprises treating said olefins with carbon monoxide and hydrogen at hydroformylation conditions in the presence of a catalyst comprising an ion exchange resin, a metal selected from the group consisting of cobalt, ruthenium, palladium, platinum and rhodium and which is directly bonded either coordinately or ionically to the ion exchange resin, and an organic linking compound which has at least one moiety coordinately bonded to the metal and further has at least one moiety which is ionically bonded to the ion exchange resin. In particular, the process will utilize, depending on the ion exchange resin, either a catalyst comprising:

(a) an ion exchange resin having a strongly acidic, weakly acidic, or mixed acid-base type functional group;

(b) a metal or element, selected from the group consisting of cobalt, ruthenium, palladium, platinum or rhodium and which is directly bonded either coordinately or ionically to the ion exchange resin; and (c) an organic linking compound of from 1 to about 100 carbon atoms which has at least one moiety selected from the group consisting of trivalent nitrogen, trivalent phosphorus, trivalent arsenic, trivalent bismuth and trivalent antimony which is coordinately bonded to said element and further has at least one moiety selected from the group consisting of monohydrocarbyl ammonium, dihydrocarbyl ammonium, trihydrocarbyl ammonium, quaternary ammonium, pyridinium, phosphonium, arsonium and sulfonium ion which is ionically bonded to the ion exchange resin or a catalyst comprising:

(1) an ion exchange resin having a basic-type functional group, (2) a metal or element selected from the group consisting of cobalt, ruthenium, palladium, platinum, and rhodium and which is directly bonded either coordinately or ionically to the ion exchange resin; and (3) an organic linking compound of from 1 to about 100 carbon atoms which has at least one moiety containing a heteroatom selected from the group consisting of trivalent nitrogen, trivalent phosphorus, trivalent arsenic, trivalent bismuth and trivalent antimony which is coordinately bonded to said element and further has at least one moiety derived from the group consisting of carboxylic acid, phosphonic acid, phosphinic acid, sulfenic acid, sulfinic acid, sulfonic acid, boronic acid and boronous acid which is ionically bonded to the ion exchange resin.

The composition of this invention and preparation thereof is described by the following illustrative embodiments which are provided for illustration and are not construed as limiting the invention.

ILLUSTRATIVE EMBODIMENTS

The catalyst preparation procedures described were carried out in nitrogen-filled dry boxes. The solvent benzene was purified by distillation over $CaH_2$, all other solvents were of reagent-grade and used as supplied. The phosphine [$(CH_3)_2NC_6H_4]_3P$, was used as supplied. The quaternized aminophosphines were prepared by reaction of one equivalent of $CH_3Br$ with an aminophosphine in toluene solution at room temperature. The quaternized aminophosphine precipitated readily from the toluene solution. The resins are indicated by (resin backbone)-(exchange group), e.g. a sulfonated styrene-divinylbenzene resin would be (styrene-divinylbenzene)-($SO_3^-$), etc. Ph, $C_6H_5$ and $\phi$-are used as abbreviations for phenyl; —$\phi$— and $C_6H_4$ indicated p-substituted benzene moieties.

PREPARATION OF THE COMPOSITIONS OF THIS INVENTION

Example 1

Preparation of carboxylated acrylic resin/Rh III.

A 10 gram quantity of carboxylated acrylic resin Bio-Rex 70 (10.2 meq/gm) was stirred with 1 liter of 1 N NaCl at room temperature for 60 minutes. The solid was collected by filtration and the procedure repeated. The material was then washed thoroughly with deionized water and 23.4 ml of a 0.5%w solution of $Rh(NO_3)_3$ in water. The combined materials were stirred overnight at room temperature. At the end of this time period, the material was collected by vacuum filtration and washed with deionized water until the washings were colorless. The material was air dried.

Example 2

Preparation of carboxylated acrylic resin/Rh III/-methyl quaternized [$(CH_3)_2NC_6H_4]_3P$ compound.

A 9.0 gram lot of the material prepared in Example 1 was added to a solution of 2 liters of acetone-water (1:1 v/v) which contained 2.0 gm (4.1 mmol) of methyl quaternized [$(CH_3)_2NC_6H_4]_3P$. These materials were stirred overnight at room temperature and the solids collected by vacuum filtration. The material was then washed with an acetone solution, a water solution, and finally air dried. The material was analyzed to contain 0.10%w Rh.

Example 3

Preparation of phosphinated styrene-divinylbenzene resin/Rh III.

A 10 gram lot of Bio Rex 63 (microreticular gel. phosphinated, 6.6 meq/gm) was treated as described in Example 1.

Example 4

Preparation of phosphinated styrene-divinylbenzene resin/Rh III/methyl quaternized [$(CH_3)_2NC_6H_4]_3P$ compound.

A 9.0 gram lot of the material prepared in Example 3 was treated with the quaternized aminophosphine as described in Example 2. Rh analysis 0.45%w.

Example 5

Preparation of sulfonated styrene-divinylbenzene resin/Rh III.

A 10 gram lot of Rohm and Haas XN1010Na (macroreticular resin, 3.6 meq/gm) was treated in a manner similar to that described in Example 1.

Example 6

Preparation of sulfonated styrene-divinylbenzene resin/Rh III/quaternized [$(CH_3)_2NC_6H_4]_3P$ compound.

A 10.0 gm lot of the material prepared in Example 5 was treated with the quaternized aminophosphine as described in Example 2. Rh analysis 0.45%w.

Example 7

Preparation of sulfonated styrene-divinylbenzene resin/[$(CH_3)_2 NC_6H_4]_3P$/platinum-tin cationic complex composition.

The aminophosphine [$(CH_3)_2NC_6H_4]_3P$ (14.0 g, 35.8 mmol) was dissolved in 1000 ml warm benzene, cooled to room temperature, and filtered into a 2-1 round-bottomed flask quickly. 10.0 G of XN1010H$^+$ ion-exchange resin was added, and the mixture stirred magnetically on side of flask for 72 hours. The resin was then filtered, washed with benzene and vacuum dried in oven (40° C.). Analysis showed a resin/ligand material having the approximate formula (styrene-divinylbenzene)-($SO_3^-$)$_{1.5}$[([$(CH_3)_2NC_6H_4]_3P)(H^+)_{1.5}$].

A $CH_2Cl_2$ solution of the platinum complex PtCl(CO) [$P(C_6H_5)_3]_2^+$ $ClO_4^-$ was prepared by the addition of 0.30 g (1.4 mmol) of anhydrous $AgClO_4$ to a solution of $PtCl_2[P(C_6H_5)_3]_2$ (1.05 g, 1.3 mmol) dissolved in 40 ml of CO-saturated $CH_2Cl_2$. The $CH_2Cl_2$ solution was stirred under 40 psi of CO for ½ hr, and filtered. To the resultant filtrate was added 5.0 g of the XN1010H$^+$ resin/ligand material prepared as described above, mixed together on a rotator for approximately 70 hours and filtered. The resultant resin material was added to a solution of 5.0 g (22.2 mmol) of $SnCl_2$. $2H_2O$ dissolved in 450 ml of acetone, mixed on rotator for 1 hour, filtered, Soxhlet-extracted with refluxing benzene for 4 hours, and dried in vacuum oven overnight at approximately 40° C. Analysis showed a composition having the approximate formula (styrene-divinylbenzene)-($SO_3$—)$_{1.5}$[([$(CH_3)_2NC_6H_4]_3$P)(H$^+$)$_{1.5}$][(PtCl(CO)[P($C_6H_5)_3]_2$)($SnCl_2$)$^+$]$_{0.07}$. The analytical results are shown in Table V below.

TABLE V

ANALYTICAL ANALYSIS OF PLATINUM-TIN/PHOSPHINE/RESIN CATALYST

| | Neutron Activation w % | Elemental wt % | Analysis Relative Molar Value (carbon = 100) |
|---|---|---|---|
| C | — | 57.8 | 100 |
| H | — | 5.56 | 116 |
| S | — | 7.05 | 4.6 |
| N | — | 1.32 | 2.0 |
| P | 1.6 | 1.59 | 1.1 |
| Sn | 7.0 | 5.82 | 1.0 |
| Cl | — | 3.55 | 2.1 |
| Pt | 2.0 | 1.83 | 0.20 |

Example 8

Preparation of sulfonated styrene-divinylbenzene resin/methylquaternized ([$(CH_3)_2NC_6H_4]_3P$/platinum-tin cationic complex composition. The quaternized aminophosphine ([$(CH_3)_2NC_6H_4]_3P)(CH_3^+)Br^-$ (10.4 g (21.1 mmol)) was dissolved in 1900 ml of an acetone/$H_2O$ (12:7 v/v) solution. 12.0 Grams of XN1010Na ion-exchange resin (prepared by exhaustive ion-exchange of XN1010H+ with 10 l of 1 N NaCl or when the pH of the effluent wash was neutral) was added. The mixture was side-stirred for 48 hours, filtered with suction, and the resin washed with 5×100 deionized $H_2O$, then vacuum dried in an oven overnight (45° C.). Analysis showed a resin/ligand material having the approximate formula (styrene-divinylbenzene)-$(SO_3^-)[([(CH_3)_2NC_6H_4]_3P)(CH_3^+)]$.

The material of this example was prepared in a similar manner as in Example 7 except that the XN1010Na resin/ligand material prepared as described above was used. Analysis showed a composition having the approximate formula (styrene-divinylbenzene)-$(SO_3^-)[([(CH_3)_2NC_6H_4]_3P)(CH_3^+)][(PtCl(CO)[P(C_6H_5)_3]_2)(SnCl_2)^+]_{0.02}$.

PROCESS UTILIZING THE COMPOSITIONS OF THIS INVENTION

Example 9

Hydroformylation of Hexene

To a 300-ml, ss Magnedrive autoclav (stirred at 600 rpm) was added 70 ml of benzene, 2.0 ml of n-decane (internal standard), 20.0 ml (160 mmol) of 1-hexene, and 1.0 g of the catalysts as listed below. The solution was deoxygenated with nitrogen. Synthesis gas ($CO/H_2$, 1:1) was then charged to the reactor and the reactor was heated to the appropriate temperature listed below. Conversions and selectivities were obtained by gas chromatography; leach rates by atomic absorption. The leach rates are extremely low, in many cases undetectable. Results are given in Table VI.

TABLE VI
HYDROFORMYLATION WITH PLATINUM/TIN CATALYSTS

| Catalyst | Temp. °C. | Pressure psig | Time hr | Conv. % |
|---|---|---|---|---|
| Example 7 | 80 | 3000 | 10 | 16.4 |
|  |  |  | 24 | 39.1 |
|  |  |  | 44 | 52.7 |
| Example 7 | 100 | 1500 | 10 | 19.3 |
|  |  |  | 24 | 35.6 |
|  |  |  | 44 | 40.0 |
| Example 7 | 100 | 3000 | 4 | 15.1 |
|  |  |  | 10.5 | 36.1 |
| Example 8 | 100 | 3000 | 20 | 21.6 |
| a | 80 | 3000 | 10 | 3.4 |
|  |  |  | 24 | 4.7 |
|  |  |  | 45 | 2.4 |

| Selectivities, % | | $C_7$-ald | Pt leach | Rate |
|---|---|---|---|---|
| $C_7$-ald | hexane | linearity (%) | ppm/hr | m/m/hr |
| 96.5 | 3.5 | 94.3 | | |
| 96.3 | 3.7 | 93.9 | | |
| 95.5 | 4.5 | 93.2 | undetectable | 170 |
| 96.3 | 3.7 | 94.0 | | |
| 94.5 | 5.2 | 93.1 | | |
| 93.5 | 6.2 | 92.4 | undetectable | 170 |
| 95.2 | 2.4 | 91.1 | | |
| 97.2 | 2.1 | 88.8 | 0.03 | 180 |
| 97.6 | 0.9 | 77.8 | undetectable | |
| 95.5 | 4.5 | 90.4 | | |
| 94.6 | 5.4 | 88.2 | — | 19 |
| 93.7 | 6.3 | 81.6 | | | a Homogeneous reaction, amount of catalyst ($PtCl_2(PΦ_3)_2$, $SnCl_2$) identical to that on Example 7 above.

Example 10

Hydroformylation of 1,5-Cyclooctadiene

To a 300-ml, ss-Magnedrive autoclave (stirred at 600 rmp) was added 15 gm (138 mmol) of 1,5-cyclooctadiene, 70 mls of THF solvent, 2 gm (10.1 mmol) of tetradecane (markert), and 0.5 gm of catalyst material. The solution was deoxygenated with nitrogen. Synthesis gas ($CO/H_2$ 1:1; 1000–1500 psig) was then charged to the reactor and the reactor was heated to 80°–90° C. Conversions and selectivities were obtained by gas chromatography; leach rates by atomic absorption spectroscopy. Results are given in Table VII.

TABLE VII
HYDROFORMYLATION OF 1,5-CYCLOOCTADIENE

| Catalyst | Time (hr) | Total Press. (psig) Ave. | Conv. (%) | 1,3-COD |
|---|---|---|---|---|
| Example 6 | 1.0 | 1300 | 17.0 | 50.8 |
|  | 2.0 |  | 34.2 | 48.7 |
|  | 3.0 |  | 80.6 | 45.5 |
|  | 4.0 |  | 96.3 | 43.2 |
|  | 5.0 |  | 99.1 | 45.6 |
| Example 6 (first recycle) | 5.0 |  | 11.8 | 61.1 |
|  | 6.0 |  | 25.7 | 65.3 |
| Example 2 | 4.0 | 1050 | 28.4 | 90.3 |
| Example 4 | 4.0 | 1000 | 18.6 | 85.2 |

| Selectivities (%) | | | Total to | Mat. Bal. | Amt. Rh. Catalyst | Leaching |
|---|---|---|---|---|---|---|
| 4-$CHOC_8$ | x-$CHOC_8$= | $CHOC_8°$ | $CHOC_8$= | (%) | (mmol) | (ppm/hr) |
| 49.2 | 0 | 0 | 49.2 | | 0.0214 | |
| 51.3 | 0 | 0 | 51.3 | | | |
| 53.5 | 1.0 | trace | 54.5 | | | |
| 52.7 | 3.7 | 0.3 | 56.4 | | | |
| 48.2 | 6.2 | 0.3 | 54.4 | 106 | | 2.5 |
| 38.9 | 0 | 0 | 38.9 | | | |
| 34.7 | 0 | 0 | 34.7 | 86 | 0.0118 | 0.17 |
| 9.7 | 0 | 0 | 9.7 | 91 | 0.534 | 0.2 |
| 14.5 | 0.4 | 0 | 14.9 | 92 | 0.0219 | 1.0 |

Illustrative Example II

Repeating the hydroformylation process of Example 9 with resin/cobalt/ligand, resin/ruthenium/ligand and resin/palladium/ligand catalysts will product substantial amounts of the $C_7$ aldehyde from the hexene.

We claim as our invention:

1. A process for hydroformylating olefins to the corresponding alcohols and/or aldehydes which comprises reacting said olefin with carbon monoxide and hydrogen at hydroformylation conditions including a temperature in the range of from about 40° to about 160° C. and a pressure in the range of from about 1 to about 500 atmospheres, in the presence of a catalyst comprising:
   (a) an ion exchange resin having a strongly acidic, weakly acidic, or mixed acid-base type functional group,
   (b) a metal selected from the group consisting of cobalt, ruthenium, palladium, platinum and rhodium and which is directly bonded either coordinately or ionically to the ion exchange resin, and
   (c) an organic linking compound of from 1 to about 100 carbon atoms which has at least one moiety which contains a heteroatom selected from the group consisting of trivalent nitrogen, trivalent phosphorus, trivalent arsenic, trivalent bismuth and trivalent antimony which is coordinately bonded to the metal and further has at least one moiety which is selected from the group consisting of monohydrocarbyl ammonium, dihydrocarbyl ammonium, trihydrocarbyl ammonium, quaternary ammonium, pyridinium, phosphonium, arsonium and sulfonium and which is ionically bonded to the ion exchange resin.

2. The process of claim 1 where, in the catalyst, the functional group of the ion exchange resin is selected from the group consisting of sulfonic acid, fluorinated alkyl sulfonic acid, phosphonic acid, carboxylic acid and aminocarboxylic acid, the ionically bonded moiety is selected from the group consisting of monohydrocarbyl ammonium, dihydrocarbyl ammonium, trihydrocarbyl ammonium, quaternary ammonium, pyridinium and phosphonium and the coordinately bonded moiety contains a heteroatom selected from the group consisting of trivalent nitrogen and trivalent phosphorus.

3. The process of claim 2 where, in the catalyst, the ion exchange resin has a back-bone selected from the group consisting of polymerized styrene, styrene-divinylbenzene, phenol-formaldehyde, benzene-formaldehyde, acrylic acid and methacrylic acid.

4. The process of claim 3 where, in the catalyst, the metal is selected from the group consisting of cobalt, platinium, and rhodium.

5. The process of claim 4 where, in the catalyst, the metal is selected from the group consisting of platinum and rhodium.

6. A process for hydroformylating olefins to the corresponding alcohols and/or aldehydes which comprises reacting said olefin with carbon monoxide and hydrogen at hydroformylation conditions including a temperature in the range of from about 40° to about 160° C. and a pressure in the range of from about 1 to about 500 atmospheres, in the presence of a catalyst comprising:
   (a) an ion exchange resin having a basic-type functional group,
   (b) a metal selected from the group consisting of cobalt, ruthenium, palladium, platinum and rhodium and which is directly bonded either coordinately or ionically to the ion exchange resin, and
   (c) an organic linking compound of from 1 to about 100 carbon atoms which has at least one moiety derived from the group consisting of carboxylic acid, phosphonic acid, phosphinic acid, sulfenic acid, sulfinic acid, sulfonic acid, boronic acid and boronous acid which is ionically bonded to said ion exchange resin and further has at least one moiety which contains a heteroatom selected from the group consisting of trivalent nitrogen, trivalent phosphorus, trivalent arsenic, trivalent bismuth and trivalent antimony which is coordinately bonded to said metal.

7. The process of claim 6 where, in the catalyst, the functional group of the ion exchange resin is selected from the group consisting of primary, secondary, tertiary, quaternary amine and pyridinium and the ionically bonded moiety is selected from the group consisting of trivalent nitrogen and trivalent phosphorus.

8. The process of claim 7 where, in the catalyst, the ion exchange resin has a backbone selected from the group consisting of polymerized styrene, styrene-divinylbenzene, phenol-formaldehyde, benzene-formaldehyde, epoxypolyamine and phenolic-polyamine.

9. The process of claim 8 where, in the catalyst, the metal is selected from the group consisting of cobalt, platinum and rhodium.

10. The process of claim 9 where, in the catalyst, the metal is selected from the group consisting of platinum and rhodium.

* * * * *